US00PP11768P2

(12) United States Plant Patent
Sorensen

(10) Patent No.: US PP11,768 P2
(45) Date of Patent: Feb. 6, 2001

(54) OSTEOSPERMUM PLANT NAMED 'BEIRA'

(75) Inventor: Carl Aksel Kragh Sorensen, Aabyhoj (DK)

(73) Assignee: Paul Ecke Ranch, Inc., Encinitas, CA (US)

( * ) Notice: Under 35 U.S.C. 154(b), the term of this patent shall be extended for 0 days.

(21) Appl. No.: 09/291,102

(22) Filed: Apr. 14, 1999

(51) Int. Cl.[7] ..... A01H 5/00

(52) U.S. Cl. ..... Plt./360

(58) Field of Search ..... Plt./360

(56) References Cited

PUBLICATIONS

UPOV CD–ROM, PBR 970699, Osteospermum designated Beira, 1997.*

* cited by examiner

*Primary Examiner*—Bruce R. Campell
*Assistant Examiner*—Melissa L. Kimball
(74) *Attorney, Agent, or Firm*—C. A. Whealy

(57) ABSTRACT

A distinct cultivar of Osteospermum plant named 'Beira', characterized by its compact, upright and very uniform plant habit; large and numerous inflorescences per plant; white ray florets with a red purple base giving the appearance of a red purple radiating ring around blue disc; inflorescences that do not close at night; and tolerance to high temperatures.

1 Drawing Sheet

BACKGROUND OF THE INVENTION

The present invention relates to a new and distinct cultivar of Osteospermum plant, botanically known as *Osteospermum ecklonis* and referred to by the cultivar name Beira.

The new cultivar is a product of a planned breeding program conducted by the Inventor in Aabyhoj, Denmark. The objective of the breeding program was to create new Osteospermum cultivars with interesting ray floret colors and heat-tolerance.

The new cultivar originated from a cross made by the Inventor in 1995 of the nonpatented *Osteospermum ecklonis* cultivar Ivory as the female, or seed, parent and a proprietary selection of *Osteospermum ecklonis* identified as 949339 as the male, or pollen, parent. The new Osteospermum was selected by the Inventor as a flowering plant within the progeny of this cross in a controlled environment in Aabyhoj, Denmark, in 1996.

Plants of the new cultivar are different from plants of the female parent, the cultivar Ivory, in plant habit, ray floret color and inflorescence form.

Plants of the new Osteospermum are different from plants of the male parent, the selection 949339, in plant habit, ray and disc color and inflorescence form.

Asexual propagation of the new cultivar by terminal cuttings at Aabyhoj, has shown that the unique features of this new Osteospermum are stable and reproduced true to type in successive generations.

SUMMARY OF THE INVENTION

The following traits have been repeatedly observed and are determined to be the unique characteristics of 'Beira'. These characteristics in combination distinguish 'Beira' as a new and distinct cultivar:

1. Compact, upright and very uniform plant habit.
2. Large and numerous inflorescences per plant.

3. White ray florets with a red purple base giving the appearance of a red purple radiating ring around blue disc.
4. Inflorescences that do not close at night.
5. Tolerance to high temperatures.

The new cultivar can be compared to the Osteospermum cultivar Cape Daisy Nairobi, disclosed in U.S. Plant Pat. No. 10,340. In side-by-side comparisons conducted in Encinitas, Calif., plants of the new cultivar are more uniform; have larger leaves; larger inflorescences; entire and more numerous ray florets; and more numerous disc florets than plants of the cultivar Cape Daisy Nairobi. In addition, plants of the cultivar Cape Daisy Nairobi do not have the red purple radiating ring surrounding the disc that plants of the new Osteospermum exhibit and also differ in coloration of ray floret lower surfaces.

The cultivar Beira has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of a typical flowering plant of 'Beira'.

The photograph at the bottom of the sheet is a close-up view of typical inflorescences, lower ray floret surfaces, and young and mature leaves of 'Beira' (code number 9602 in the photograph) and 'Cape Daisy Nairobi' (Nairobi in the photograph). Foliage and floret colors in the photographs may appear different from the actual colors due to light reflectance.

DETAILED BOTANICAL DESCRIPTION

The following observations, measurements and values describe plants of the new cultivar grown in a 10-cm hanging basket in Encinitas, Calif., under outdoor, full-sun conditions with day temperatures ranging from 20 to 27° C. and night temperatures ranging from 6 to 14° C. Plants were pinched (terminal apex removed) one time about two weeks after planting rooted cuttings. Plants used for this description were grown for about 12 to 14 weeks after planting rooted cuttings.

Color references are made to The Royal Horticultural Society Colour Chart except where general terms of ordinary dictionary significance are used.

Botanical classification: *Osteospermum ecklonis* cultivar Beira.

Parentage:

*Female, or seed, parent.*—*Osteospermum ecklonis* cultivar Ivory, not patented.

*Male, or pollen, parent.*—Proprietary selction of *Osteopermum ecklonis* identified as 949339.

Propagation:

*Type.*—By terminal cuttings.

*Time to initiate roots.*—About 10 days at 18° C.

*Time to develop roots.*—About 21 days at 18° C.

*Rooting habit.*—Fibrous.

Plant description:

*Appearance.*—Perennial herbaceous container and garden plant. Inverted triangle. Upright and very uniform growth habit; flat to rounded canopy. Freely branching with about 7 primary and about 18 secondary branches. Full plants with dense foliage and erect flower stems.

*Vigor.*—Vigorous.

*Plant height.*—About 44 cm.

*Plant spread.*—About 40 cm.

*Lateral branch description.*—Length: About 17 to 20 cm. Diameter: Primary, about 8 mm; secondary, about 4 mm. Internode length: About 1.5 to 2 cm. Texture: Short coarse hairs; woody at base. Color: 144A.

*Foliage description.*—Leaves alternate, single. Quantity of leaves per secondary branch: Numerous, about 34. Length, fully expanded leaves, basal: About 8.5 to 9 cm. Width, fully expanded leaves, basal: About 3 to 3.2 cm. Shape: Elliptic to lanceolate. Apex: Broadly acute. Base: Attenuate. Margin: Nearly entire with five to seven widely-spaced irregular teeth. Teeth typically present on older leaves. Aspect: Mostly flat. Texture: Smooth; thick and leathery; slightly pubescent on lower surface. Color: Young foliage, upper surface: 137A. Young foliage, lower surface: 137B. Fully expanded foliage, upper surface: 137A. Fully expanded foliage, lower surface: 137B. Attenuated leaf base: 137D. Venation, upper and lower surfaces: 137D.

Inflorescence description:

*Appearance.*—Daisy-type composite infloresence form; actinomorphic. Single inflorescences displayed at or just above foliage, upright on long peduncles arising from leaf axils. Disc and ray florets arranged acropetally on a capitulum. Typically about 71 opened and unopened inflorescences per plant. Inflorescences last about one week. Inflorescences persistent. Inflorescences not night-closing.

*Flowering response.*—Plants flower continuously from April to October in the Northern Hemisphere.

*Fragrance.*—None detected.

*Inflorescence size.*—Diameter: About 8 to 8.5 cm. Depth (height): About 1.5 cm. Diameter of disc: About 1.6 cm.

*Inflorescence buds.*—Length: About 2 cm. Width: About 1.3 cm. Shape: Ovoid. Color: 147A.

*Ray florets.*—Length: About 3.8 cm. Width: About 1 cm. Shape: Ligulate; under certain environmental conditions spoon shaped ray florets may be occasionally observed. Apex: Tri-dentate, minute. Base: Acute. Margin: Entire. Aspect: Flat, slightly reflexed. Texture: Smooth, satiny. Number of ray florets per inflorescence: About 24 in two whorls. Color: When opening, upper surface: 155C. When opening, lower surface: Longitudinally striped, grayed purple, more gray than 83C, with yellow green, 151C. Fully opened, upper surface: White, 155D, with red purple, 87A to 87B, at base and on proximal margin giving the appearance of a red purple radiating ring around blue disc. Fully opened, lower surface: Longitudinally striped, light tan/orange, 168D, with grayed green, close to 194A; base, lavender, 83D.

*Disc florets.*—Shape: Tubular; salverform; five-lobed, fluted at apex. Number of disc florets per inflorescence: Numerous, about 128. Length: About 5 mm. Width: About 2 mm. Color: Immature: Apex, 86A; midsection, 86D. Mature: Apex, 86A; midsection, 84A.

*Phyllaries.*—Shape: Linear. Apex: Narrowly acute. Margin: Entire. Quantity and arrangement: About 20 to 22 per inflorescence; whorled. Texture: Hirsute. Color: Upper surface: 138C. Lower surface: 138A.

*Peduncle.*—Length: About 7 cm. Aspect: Strong; inflorescences held above foliage. Texture: Hispid; coarse. Color: 144A.

*Reproductive organs.*—Androecium: Present on disc florets only. Stamens: Five; fused. Anther shape: Oblong. Anther size: About 2 mm. Anther color: 79A. Pollen amount: Abundant. Pollen color: 14A. Gynoecium: Present on ray and disc florets. Pistils: One. Pistil length: About 4 mm. Stigma shape: Bipartate. Stigma color: 79A. Style length: About 3 mm. Style color: 79A. Ovary color: 144C. Seed: Seed development has not been observed.

Disease resistance: Resistance to pathogens common to Osteospermum has not been observed on plants of the new Osteospermum.

Heat tolerance: Plants of the new Osteospermum have demonstrated good tolerance to high temperatures.

It is claimed:

1. A new distinct cultivar of Osteospermum plant named 'Beira', as illustrated and described.

* * * * *

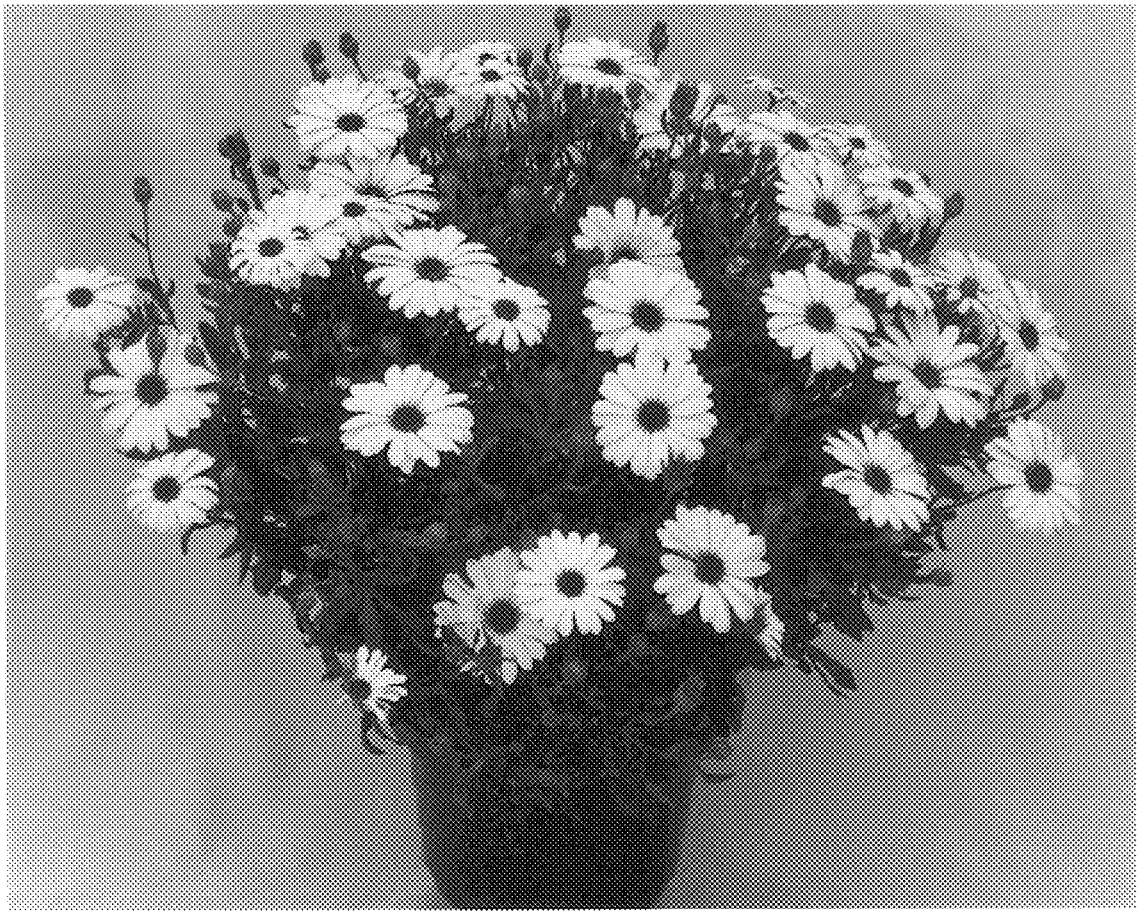
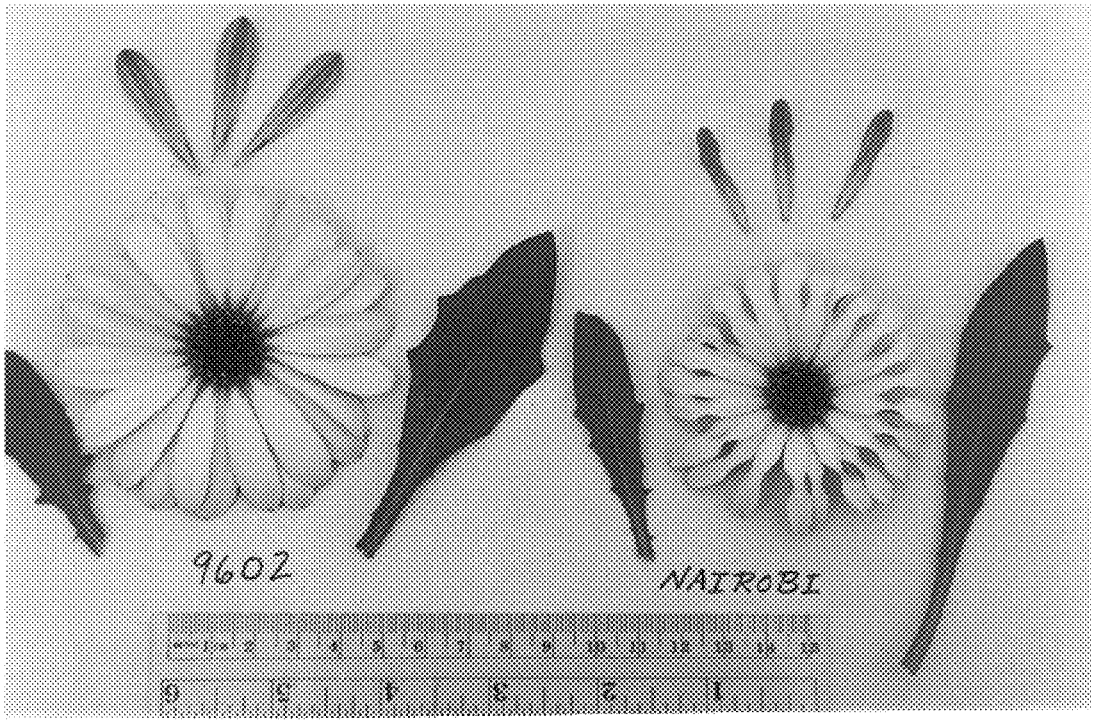
9602
NAIROBI